US008597668B2

(12) United States Patent
Nguyen et al.

(10) Patent No.: US 8,597,668 B2
(45) Date of Patent: Dec. 3, 2013

(54) CLEAR CARRIER COMPOSITIONS FOR LIPOPHILIC COMPOUNDS, AND METHOD OF TREATING KERATINOUS SUBSTRATES USING SUCH COMPOSITIONS

(75) Inventors: Nghi Van Nguyen, Edison, NJ (US); Sawa Hashimoto, Westfield, NJ (US); David W. Cannell, New Hope, PA (US)

(73) Assignee: L'Oreal, Paris (FR)

( * ) Notice: Subject to any disclaimer, the term of this patent is extended or adjusted under 35 U.S.C. 154(b) by 332 days.

(21) Appl. No.: 12/701,195

(22) Filed: Feb. 5, 2010

(65) Prior Publication Data

US 2010/0203000 A1     Aug. 12, 2010

Related U.S. Application Data

(60) Provisional application No. 61/150,847, filed on Feb. 9, 2009, provisional application No. 61/150,848, filed on Feb. 9, 2009, provisional application No. 61/150,852, filed on Feb. 9, 2009, provisional application No. 61/150,849, filed on Feb. 9, 2009.

(51) Int. Cl.
*A61K 8/02* (2006.01)

(52) U.S. Cl.
USPC ........ 424/401; 424/70.17; 510/499; 514/546; 514/552; 522/126; 522/130

(58) Field of Classification Search
None
See application file for complete search history.

(56) References Cited

U.S. PATENT DOCUMENTS

| | | | |
|---|---|---|---|
| 4,488,564 A | 12/1984 | Grollier | |
| 5,223,244 A | 6/1993 | Moro | |
| 5,853,705 A | 12/1998 | Nakayama | |
| 5,866,144 A | 2/1999 | Chopra | |
| 6,191,083 B1 | 2/2001 | Brooks | |
| 6,218,345 B1 | 4/2001 | Brooks | |
| 6,419,962 B1 | 7/2002 | Yokohama-Shi | |
| 6,426,063 B1 | 7/2002 | Schuler | |
| 6,946,124 B2 | 9/2005 | Arnaud-Sebillotte | |
| 7,147,873 B2 | 12/2006 | Scholz | |
| 7,157,413 B2 | 1/2007 | Lazzeri | |
| 7,323,163 B2 | 1/2008 | Wang | |
| 2002/0006389 A1 | 1/2002 | Restle | |
| 2002/0010215 A1 | 1/2002 | Shiroyama | |
| 2002/0034489 A1 | 3/2002 | Wiegand | |
| 2002/0193265 A1 | 12/2002 | Perron | |
| 2003/0091602 A1* | 5/2003 | Witteler et al. | 424/401 |
| 2004/0033984 A1 | 2/2004 | Muller | |
| 2004/0185020 A1 | 9/2004 | Gawtrey | |
| 2004/0266886 A1 | 12/2004 | Seipel | |
| 2005/0031566 A1 | 2/2005 | Cooper | |
| 2005/0032668 A1 | 2/2005 | Pedersen | |
| 2005/0084471 A1 | 4/2005 | Andrews | |
| 2005/0089539 A1 | 4/2005 | Scholz | |
| 2006/0051384 A1 | 3/2006 | Scholz | |
| 2006/0051385 A1 | 3/2006 | Scholz | |
| 2006/0052452 A1 | 3/2006 | Scholz | |
| 2006/0159782 A1 | 7/2006 | Amano | |
| 2006/0286057 A1 | 12/2006 | Cannell et al. | |
| 2008/0038215 A1 | 2/2008 | Derici | |
| 2008/0085258 A1 | 4/2008 | Nguyen et al. | |
| 2009/0202465 A1 | 8/2009 | Mougin et al. | |
| 2010/0202988 A1 | 8/2010 | Nguyen et al. | |
| 2010/0202995 A1 | 8/2010 | Nguyen et al. | |
| 2010/0202999 A1 | 8/2010 | Nguyen et al. | |
| 2010/0203000 A1 | 8/2010 | Nguyen et al. | |

FOREIGN PATENT DOCUMENTS

| | | | |
|---|---|---|---|
| EP | 510879 A3 | 3/1993 | |
| EP | 0532272 A3 | 3/1993 | |
| EP | 1213007 A3 | 6/2002 | |
| EP | 1535602 A1 | 6/2005 | |
| EP | 1739161 A1 | 4/2009 | |
| JP | 2003105669 A | 4/2003 | |
| JP | 2006028096 A | 2/2006 | |
| WO | 98/00494 A1 | 1/1998 | |
| WO | 2006/010440 A1 | 2/2006 | |
| WO | 2006/010441 A1 | 2/2006 | |
| WO | 2006/045418 A1 | 5/2006 | |
| WO | 2006/099358 A3 | 9/2006 | |
| WO | WO 2007/003784 A1 | 1/2007 | |

OTHER PUBLICATIONS

Tsiourvas, D.; Arkas, M.; Paleos, C. M.; Skoulios, A. "Smectic mesomorphism of long-chain n-Alkylammonium polyacrylates" Polymer Preprints (American Chemical Society, Division of Polymer Chemistry) (1997), 38(1), p. 233-234.

John A. Wenninger, G.N. McEwen, Jr., International Cosmetic Ingredient Dictionary and Handbook, 1997, 7th Edition, published by The Cosmetic, Toiletry and Fragrance Association Inc. (CTFA), 1101 17th Street, N.W., Suite 300, Washington, DC, USA.

Ernest W. Flick, "Anti-Frizz Formulas with PrimaFlo HP-22 (Formulation A)", Cosmetics and Toiletries Formulations Database, 2005, William Andrew Publishing.

Ernest W. Flick, Cosmetics Additives an Industrial Guide, Noyes Publications.

Lupasol Product Range: Preliminary Technical Information, Sep. 1996, BASF.

Zhongshan Kemei Oleochemicals Co., Ltd (http://daily-chemical-raw-materials.com/products; downloaded Nov. 16, 2012).

* cited by examiner

*Primary Examiner* — Hasan Ahmed
(74) *Attorney, Agent, or Firm* — L'Oreal USA

(57) ABSTRACT

The present invention relates to a composition comprising:

(a) at least one alkoxylated polyamine;

(b) at least one organic acid chosen from alkyl acids, alkoxylated monoacids, and mixtures thereof;

(c) at least one lipophilic compound; and (d) at least one solvent comprising water.

Such a composition is clear in appearance, and stable.

The present invention also relates to a method of making such a clear composition, and to a method of cosmetic treatment of a keratinous substrate using such a composition.

33 Claims, No Drawings

CLEAR CARRIER COMPOSITIONS FOR LIPOPHILIC COMPOUNDS, AND METHOD OF TREATING KERATINOUS SUBSTRATES USING SUCH COMPOSITIONS

REFERENCE TO PRIOR APPLICATIONS

This application claims the benefit of priority under 35 U.S.C. §119(e) from U.S. provisional application Ser. Nos. 61/150,847, 61/150,848, 61/150,852 and 61/150,849, filed Feb. 9, 2009, incorporated herein by reference in their entirety.

TECHNICAL FIELD

The present invention relates to carrier compositions comprising lipophilic ingredients. More particularly, the present invention provides for a clear composition containing one or more lipophilic ingredients, which remains clear even when diluted in particular with water.

The invention further relates to methods of treating keratinous substrates using such compositions.

BACKGROUND OF THE DISCLOSURE

Cosmetic and personal care products are available in various forms and one of the forms that are desired by many consumers is a clear aqueous product. At the same time, the consumer expects that such a product will provide desirable cosmetic benefits to keratinous substrates such as hair and skin.

These cosmetic benefits can be provided by the presence of water-insoluble ingredients, for example, oils, silicones and other lipophilic materials, in the product.

However, certain water-insoluble ingredients, which are oftentimes desirable for the treatment of keratinous substrates, are inherently difficult to incorporate into aqueous systems, such as shampoos, conditioners and skin care compositions, without forming a traditional emulsion in either cream or lotion form. Oftentimes, the presence of such ingredients at levels that would impart appreciable cosmetic benefits to hair or skin and/or properties to cosmetic and personal care products results in unstable formulations resulting in undesirable phase separations in aqueous systems.

Therefore, in the formulation of clear aqueous compositions, water-insoluble compounds do not lend themselves to being used therein, due to their inability to significantly associate with the water present in the system. As a result, the presence of these water-insoluble ingredients is generally minimal in personal care products and cosmetic products that employ aqueous systems. Thus, the difficulties in formulating such compositions deprives the consumer of products that can better deliver cosmetic benefits to hair and skin such as conditioning, cleansing, coloring of hair, styling of hair, skin care, and better application and spreadability of products.

Thus, there remains a need for an aqueous composition which can carry increased amounts of water-insoluble materials while remaining both homogeneous and clear in appearance. There also remains a need for an aqueous system which can carry increased amounts of water-insoluble materials such as oils and other lipophilic ingredients in order to deliver desirable benefits to hair and skin.

It has been surprisingly and unexpectedly discovered that the combination of at least one alkoxylated polyamine, at least one organic acid chosen from alkyl acids, alkoxylated monoacids and mixtures thereof, at least one solvent, and at least one water-insoluble compound such as a lipophilic compound, yields a composition which is clear in appearance and stable. Moreover, the inventive composition remains clear and stable even if additional solvent such as in particular water is added thereto.

It has also been discovered that the use of this clear composition on keratinous substrates, such as hair and skin, results in desirable and beneficial effects on the substrates, such as in particular improved delivery of active ingredients, improved cosmetic effects such as improved color retention on colored-treated hair, improved conditioning, improved hair styling effects and manageability, improved shine, improved protection from environmental and chemical damage, and enhanced color is the case of coloring compositions.

BRIEF SUMMARY OF THE DISCLOSURE

The present invention is directed to a composition comprising:
 (a) at least one alkoxylated polyamine;
 (b) at least one organic acid chosen from alkyl acids, alkoxylated monoacids, and mixtures thereof;
 (c) at least one lipophilic compound; and
 (d) at least one solvent comprising water.
Such a composition is clear in appearance, and stable.

The present invention is also directed to a method of making a clear composition involving the steps of:
 (a) providing at least one alkoxylated polyamine;
 (b) providing at least one organic acid chosen from alkyl acids, alkoxylated monoacids, and mixtures thereof;
 (c) providing at least one lipophilic compound;
 (d) providing at least one solvent comprising water; and
 (e) mixing the compounds as defined in steps (a) to (d) to form a composition that is clear in appearance.

The present invention is further directed to a method of cosmetic treatment of a keratinous substrate involving the step of applying onto said keratinous substrate a composition as defined herein.

DETAILED DESCRIPTION OF THE DISCLOSURE

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about".

The term "lipophilic" means those compounds which are soluble in oils and either completely or partially insoluble in water. In accordance with the present invention, the lipophilic compounds preferably have a solubility in water at 25° C. and at atmospheric pressure of less than 5% by weight, more preferably less than 1% by weight, even more preferably less than 0.5% by weight and better still less than 0.1% by weight.

"At least one" as used herein means one or more and thus includes individual components as well as mixtures/combinations thereof.

The term "clear" as used herein means transparent such that a person is able to see through the composition with their naked eye. The term "clear" as used herein is not meant to encompass those compositions which a person cannot see through with their naked eye such as those which are pearlescent, frosted, hazy, opaque, or cloudy in appearance.

The clarity of the compositions of the present invention can be determined using the McFarland scale, which is based on the McFarland Equivalence Turbidity Standard Test (Remel, 12076 Santa Fe Drive, Lenexa, Kans. 66215, USA). Preferably, the compositions according to the present invention have a McFarland turbidity standard value, as visually determined, equal to or less than 0.5 on the McFarland scale.

The term "stable" as used herein means that the composition does not exhibit phase separation.

The term "carrier system for lipophilic compounds" means a system that delivers a lipophilic ingredient into an aqueous phase by incorporation or solubilization. The lipophilic carrier system of the present invention is capable of bringing lipophilic compounds into an aqueous phase such that the aqueous phase remains clear and stable.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Alkoxylated" as used herein means comprising at least one alkoxy group. As used herein, an alkoxy group is a group corresponding to the formula —O—CHR—(CH2)$_n$—, wherein R represents H or a C1-C5 alkyl group, and wherein n is an integer ranging from 1 to 6.

Alkoxylated Polyamines

Non-limiting preferred examples of suitable alkoxylated polyamines include hydrocarbyl amines which have at least one primary nitrogen atom and include compounds corresponding to formula (I):

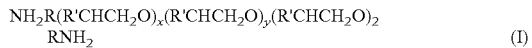

wherein R represents a —CHCH$_3$— or —C(CH$_3$)$_2$— group, or a hydrocarbon radical containing at least 3 carbon atoms that can be linear or branched, acyclic or cyclic, saturated or unsaturated, aliphatic or aromatic, substituted or unsubstituted;
x, y, and z independently of one another, represent numbers of from 0 to 100;
R' represents hydrogen, or an alkyl group, preferably a methyl group; and
the sum of x+y+z is at least 1.

In formula (I), R is preferably a linear or branched, acyclic alkyl or alkenyl group or an alkyl phenyl group; x, y, and z independently of one another, preferably represent numbers ranging from 2 to 100.

Examples of the alkoxylated polyamines for use in the present invention which correspond to formula (I) include, for example, tetradecyloxypropyl-1,3-diaminopropane; C$_{12\text{-}14}$ alkyl oxypropyl-1,3-diaminopropane; C$_{12\text{-}15}$ alkyloxypropyl amine and other similar materials that are commercially available from Tomah under the tradename of TOMAH® DA-17.

Other examples of alkoxylated polyamines of Formula (I) are diamine compounds belonging to the Jeffamine series such as the Jeffamine® D and Jeffamine® ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. Jeffamine® D series compounds are amine terminated PPGs (polypropylene glycols) and Jeffamine® ED series compounds are polyether diamine based with a predominantly PEG (polyethylene glycol) backbone.

Other non-limiting preferred examples of suitable alkoxylated polyamines in the diamine form include compounds corresponding to formula (II):

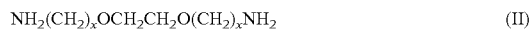

wherein x is 2 or 3.

Examples of alkoxylated polyamines of Formula (II) are diamine compounds belonging to the JEFFAMINE series available from Huntsman Corporation, Salt Lake City, Utah, such as JEFFAMINE EDR148, and JEFFAMINE EDR176.

Additional non-limiting preferred examples of alkoxylated polyamines in the triamine form include compounds corresponding to formula (III):

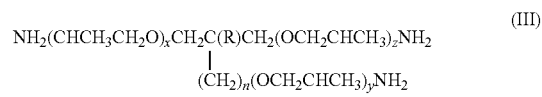

wherein R is hydrogen or —C$_2$H$_5$,
n=0 or 1, and
x, y, and z independently of one another, represent numbers of from 0 to 100 and the sum of x+y+z is at least 1.

Examples of alkoxylated polyamines for use in the present invention which correspond to formula (III) are triamine compounds belonging to the Jeffamine series such as the Jeffamine® T series available from Huntsman Corporation, Salt Lake City, Utah. Examples of the Jeffamine® T series compounds are JEFFAMINE T403, JEFFAMINE T3000, and JEFFAMINE T5000. Jeffamine® T series compounds are triamines made by reacting PO with a triol initiator followed by aminating the terminal hydroxyl groups.

Another type of preferred alkoxylated polyamines include compounds of formulas (IV) and (V) hereunder:

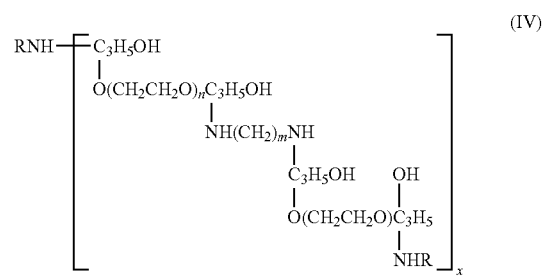

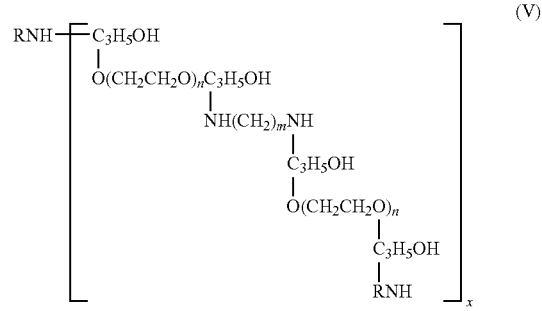

wherein
R in formula (IV) represents the alkyl group derived from tallow and R in formula (V) represents the alkyl group derived from coconut oil;
n in both formulas (IV) and (V) has a total value ranging from 10 to 20;
m in both formulas (IV) and (V) has a value ranging from 2 to 6; and
x in both formulas (IV) and (V) has a value ranging from 2 to 4.

Examples of alkoxylated polyamines of Formulas (IV) and (V) are PEG-15 Tallow Polyamine and PEG-15 Cocopolyamine, respectively.

The at least one alkoxylated polyamine is present in the composition of the present invention a preferred amount ranging from 0.1 to 50% by weight, preferably from 0.5 to 15% by weight, more preferably from 0.5 to 10% by weight, based on the total weight of the composition.

Alkyl Acids

The at least one alkyl acid of the composition of the present invention is preferably chosen from fatty monocarboxylic acids, fatty phosphoric acids and mixtures thereof.

By "fatty", it is meant that such acids contain a fatty chain having at least 6 carbon atoms, preferably from 8 to 30 carbon atoms.

Non-limiting preferred examples of fatty monocarboxylic acids include fatty acids corresponding formula (IA):

$$RCOOH \qquad (IA)$$

wherein R is a hydrocarbon radical containing at least 6 carbon atoms, preferably from 8 to 30 carbon atoms, more preferably from 12 to 24 carbon atoms. R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group.

Suitable fatty acids include, but are not limited to the following examples: arachidic acid, arachidonic acid, beeswax acid, capric acid, caproic acid, caprylic acid, coconut acid, isostearic acid, lauric acid, linoleic acid, linolenic acid, myristic acid, oleic acid, olive acid, palmitic acid, rapeseed acid, stearic acid, behenic acid, tallow acid, undecanoic acid, undecylenic acid, wheat germ acid and mixtures thereof.

Preferred fatty acids in the present invention include capric acid, linoleic acid, oleic acid, isostearic acid, stearic acid and mixtures thereof.

Non-limiting preferred examples of fatty phosphoric acids include compounds corresponding to Formula (IIA):

$$R-O-P(O)(OH)_2 \qquad (IIA)$$

wherein R is a hydrocarbon radical containing at least 6 carbon atoms, preferably from 8 to 30 carbon atoms, more preferably from 12 to 24 carbon atoms. R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group.

Typical suitable fatty phosphoric acids include capryl phosphate, caprylyl phosphate, lauryl phosphate, oleyl phosphate, isostearyl phosphate, stearyl phosphate, cetyl phosphate and mixtures thereof.

Alkoxylated Monoacids

Non-limiting preferred examples of alkoxylated monoacids include compounds corresponding to formula (IB):

$$RO[CH_2O]_u[(CH_2)_xCH(R')(CH_2)_yO]_v[CH_2CH_2O]_w \\ CH_2COOH \qquad (IB)$$

wherein:
R is a hydrocarbon radical containing from 6 to 40 carbon atoms, preferably from 8 to 30 carbon atoms, more preferably from 12 to 24 carbon atoms;
u, v and w, independently of one another, represent numbers of from 0 to 60, provided that the sum u+v+w is greater than 0;
x and y, independently of one another, represent numbers of from 0 to 13, where the sum x+y is greater than or equal to 0;
R' represents hydrogen or an alkyl group, and preferably a methyl group.

Compounds corresponding to formula (IB) can be obtained by alkoxylation of alcohols of formula ROH—with R as defined in formula (IB)—with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (IB), R is linear or branched, acyclic or cyclic, saturated or unsaturated, aliphatic or aromatic, substituted or unsubstituted. Typically, R is a linear or branched, acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group, and even more typically a $C_{12-18}$ alkyl group or alkenyl group or a $C_{6-16}$ alkyl phenyl group;
the sum u+v+w, is preferably a number ranging from 2 to 20, more preferably a number ranging from 3 to 17 and most preferably a number from 5 to 15;
the sum x+y is typically a number from 1 to 13, more preferably a number from 1 to 10.

Suitable alkoxylated monoacids of the present invention include, but are not limited to, the following representatives referred to by their INCI names (INCI: nomenclature for raw materials according to the International Cosmetic Ingredient Dictionary, 7$^{th}$ Edition, published by the Cosmetic, Toiletry and Fragrance Association Inc. (CTFA), Washington D.C., USA): Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, $C_{9-11}$ Pareth-6 Carboxylic Acid, $C_{11-15}$ Pareth-7 Carboxylic Acid, $C_{12-13}$ Pareth-5 Carboxylic Acid, $C_{12-13}$ Pareth-8 Carboxylic Acid, $C_{12-13}$ Pareth-'12 Carboxylic Acid, $C_{12-15}$ Pareth-7 Carboxylic Acid, $C_{12-15}$ Pareth-8 Carboxylic Acid, $C_{14-15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof.

The at least one organic acid chosen from alkyl acids, alkoxylated monoacids and mixtures thereof is preferably present in the composition in an amount of from 0.1 to 50% by weight, preferably from 0.5 to 30% by weight, and more preferably 1 to 20% by weight, based on the total weight of the composition.

Preferably, the ratio of the amine number of the at least one alkoxylated polyamine to the total acid number of organic acid(s) chosen from alkyl acids, alkoxylated monoacids and mixtures thereof, is from 1:10 to 10:1, more preferably from 1:5 to 5:1, and even more preferably from 1:2 to 2:1. Also, the composition remains clear when diluted with any ratio or amount of additional solvent.

Acid and amine numbers are generally determined by acid-base titration in the presence of a color indicator based on the European and American Pharmacopoeias and Standard ISO 660.

Lipophilic Compound

The at least one lipophilic compound may, for example, be chosen from oils, fatty esters, hydrocarbon oils, silicones, waxes, fatty alcohols, lipophilic vitamins and esters thereof, organic sunscreens, phospholipids, and mixtures thereof.

Non-limiting examples of oils include plant oils such as olive oil, avocado oil, coconut oil, safflower oil, almond oil, castor oil, jojoba oil, peanut oil, sesame oil, hazelnut oil, sunflower oil, apricot kernel oil, grapeseed oil, linseed oil and palm oil.

Non-limiting examples of hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, and mixtures thereof.

Non-limiting examples of silicones include phenyltrimethicone, dimethicone, cyclomethicone, dimethicone copolyol, aminosilicone, laurylmethicone copolyol, cetyl dimethicone, cetyl triethylammonium dimethicone copolyol phthalate, dimethicone copolyol lactate, silicone quaternium 13, stearalkonium dimethicone copolyol phthalate, stearamidopropyl dimethicone and polyorganosiloxanes such as polydimethylsiloxane.

Non-limiting examples of waxes include paraffin wax, beeswax, candelilla wax, carnauba wax, jasmine wax, jojoba wax and mimosa wax.

Non-limiting preferred examples of fatty alcohols include compounds of formula:

R—OH where R represents a hydrocarbon radical containing at least three carbon atoms, preferably from 8 to 30, more preferably from 12 to 24 carbon atoms, and which may be linear or branched, acyclic or cyclic, saturated or unsaturated, aliphatic or aromatic, substituted or unsubstituted. Typically, R is a linear or branched, acyclic alkyl or alkenyl group or an alkyl phenyl group.

Non-limiting preferred fatty esters include esters formed from $C_{8-30}$ fatty acids and $C_{1-10}$ alcohols and esters formed from the fatty alcohols as defined hereabove and $C_{1-10}$ carboxylic acids.

According to a preferred embodiment, the at least one lipophilic compound is chosen from isopropyl palmitate, capric/caprylic triglyceride, isodecyl neopentanoate, polylsobutylene, phloretin, ellagic acid, vitamin D, vitamin E, vitamin E acetate, vitamin A, vitamin A palmitate, 2-oleamido-1,3-octadecanediol, octyl methoxycinnamate, octyl salicylate, 18-methyleicosanoic acid, and mixtures thereof.

The at least one lipophilic compound is present in the composition in a preferred amount of from 0.1 to 50% by weight, more preferably from 0.1 to 30% by weight, and even more preferably from 0.5 to 15% by weight, based on the total weight of the composition.

Solvent

The solvent is typically present in an amount from 10 to 95% by weight, preferably from 50 to 85% by weight, and more preferably from 60 to 80% by weight, based on the total weight of the composition. The solvent comprises water such as deionized water, alone or in combination with at least one $C_1$-$C_4$ alcohol. Alcohols include ethanol, propanol and butanol. Preferably, the alcohol is chosen from ethanol, isopropanol and mixtures thereof.

The solvent preferably comprises at least 20% by weight of water, more preferably at least 50% by weight, even more preferably at least 80% by weight, based on the total weight of the solvent.

Auxiliary Ingredients

The composition may optionally contain at least one auxiliary ingredient. The auxiliary ingredients may include in particular film forming agents, proteins, amino acids, cationic conditioners, cationic polymers, nonionic surfactants, anionic surfactants, amphoteric surfactants, zwitterionic surfactants, viscosity modifiers, antibacterial agents, sunscreens, preservatives, pH adjusting agents, bleaching agents, hair dyeing agents, perfumes, sequestering agents, anti-dandruff agents, alpha or beta hydroxy acids or alpha ketoacids, and mixtures thereof.

Non-limiting examples of film forming agents can be chosen from anionic compounds, non-ionic compounds, amphoteric compounds, zwitterionic compounds, proteins, viscosity modifiers, cationic polymers, polyamides, polyaminoamides, polyesters, silicone resins, polysaccharides, silicone fluids, polyacrylamides, starches, gums and mixtures thereof.

Non-limiting examples of proteins include collagen, deoxyribonuclease, iodized corn protein, milk protein, protease, serum protein, silk, sweet almond protein, wheat germ protein, wheat protein, alpha and beta helix of keratin proteins, hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Non-limiting examples of amino acids include amino acids derived from the hydrolysis of various proteins as well as the salts, esters, and acyl derivatives thereof. Non-limiting examples of such amino acid agents include amphoteric amino acids such as alkylamido alkylamines, i.e. stearyl acetyl glutamate, capryloyl silk amino acid, capryloyl collagen amino acids, capryloyl keratin amino acids, capryloyl pea amino acids, cocodimonium hydroxypropyl silk amino acids, corn gluten amino acids, cysteine, glutamic acid, glycine, hair keratin amino acids, amino acids such as asparatic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline, lysine, silk amino acids, wheat amino acids and mixtures thereof.

Non-limiting examples of cationic conditioners include quaternium-27, behenamidopropyl PG-dimonium chloride, hydroxyethyl tallowedimonium chloride, stearalkonium chloride and cetrimonium chloride.

Non-limiting examples of cationic polymers include hexadimethrine chloride, polyquaternium-4, polyquaternium-6, polyquaternium-7, polyquaternium-10, polyquaternium-11, polyquaternium-16, polyquaternium-22 and polyquaternium-32.

Non-limiting examples of nonionic surfactants includes alkoxylated derivatives of the following: fatty alcohols, alkyl phenols, fatty acid esters and fatty acid amides, wherein the alkyl chain is in the $C_{12-50}$ range, typically in the $C_{16-40}$ range, more typically in the $C_{24}$ to $C_{40}$ range, and having from 1 to 110 alkoxy groups. The alkoxy groups are selected from the group consisting of $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated fatty alcohols are preferred, and the ethoxylated alcohols and propoxylated alcohols are more preferred. The alkoxylated alcohols may be used alone or in mixtures with those alkoxylated materials disclosed hereinabove.

Representative preferred examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10), steareth-10 (a stearyl alcohol ethoxylate having an average degree of ethoxylation of 10), steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and mixtures of the precedings.

Commercially available corresponding nonionic surfactants are for example Brij® nonionic surfactants from Croda, Inc., Edison, N.J. Typically, Brij® is the condensation products of aliphatic alcohols with from 1 to 54 moles of ethylene oxide, the alkyl chain of the alcohol being typically a linear chain and having from 8 to 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from 1 to 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from 1 to 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being typical. Nonlimiting examples of commercially available ethoxylated materials include ethoxylated sorbitan mono-, di- and/or tri-esters of $C_{12}$ to $C_{18}$ fatty acids with an average degree of ethoxylation of from 2 to 20, such as the products sold under the name TWEEN® by the company Uniqema.

Non-limiting examples of anionic surfactants include compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, succinamates, sulfosuccinates, sarcosinates, octoxynol or nonoxynol phosphates, taurates, fatty taurides, sulfated monoglycerides, fatty acid amino polyoxyethylene sulfates, isethionates and mixtures thereof. Specific examples of anionic surfactants include the ammonium, monoethanolamine, diethanolamine, triethanolamine, isopropylamine, sodium, potassium, lithium, or magnesium salts of lauryl sulfate, dodecylbenzene-sulfonate, lauryl sulfosuccinate, lauryl ether sulfate, lauryl sarcosinate, cocomethyl tauride, and sulfosuccinate half ester amide and mixtures thereof.

Non-limiting examples of amphoteric and zwitterionic surfactants include alkyl, alkyl dimethyl, alkylamido, alkyl amide, alkylamidopropyl, or alkyl dimethylammonium betaine; alky amidopropyl or alkyl sulfobetaine; alkyl, alkylampho, or alkylamphocarboxy glycinate; alkyl, or alkyl substituted imidazoline mono or dicarboxylate; sodium salts of alkyl mono- or dicarboxylates; alkyl beta amino acids; alkyl amidopropyl, or alkyl ether hydroxysultaine; alkyl amidopropyl dimethyl ammonia acetate; alkyl ampho mono- or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures.

Specific examples include cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate and mixtures thereof.

Non-limiting examples of viscosity modifiers include water swellable/soluble cationic polymers from quaternized polysaccharides such as trimethyl ammonium substituted epoxide of hydroxyethyl cellulose, diallyldimethyl ammonium salts of hydroxyethylcellulose, deacylated chitin or chitosan, dihydroxypropyl chitosan trimonium chloride, hydroxypropltrimethyl ammonium chloride guar, locust bean, or konjac mannan gum; quaternized synthetics such as acrylamide dimethyl diallyl ammonium chloride copolymers, acrylamide/dimethyl diallyl ammonium chloride/acrylic acid terpolymer, quaternized poly(vinyl pyrrolidone/dimethyl amino ethylmethacrylate), poly (vinylpyrrolidone/methacrylamidopropyl trimethylammonium chloride), polyvinyl pyrrolidone/methylvinylimidazolinium chloride or methyl sulfate copolymer, chloroethylether/dimethylaminopropylamine/adipate or azelate terpolymer, vinylpyrrolidone/methacrylamidopropyl trimethylammonium chloride, acrylonitrile/acrylic acid/dimethylpropanediammonium acrylates sulfate terpolymer.

Further suitable viscosity modifiers include anionic or nonionic polysaccharide polymers such as gum tragacanth, sodium or propylene glycol alginate, kappa-, iota-, or lambda-carrageenan, guar or hydroxyl propyl guar gum, karaya gum, gum arabic, locust bean gum, konjac mannan gum, gellan, xanthan, succinoglycan or its acidic or enzymatic hydrolysates, sodium carboxymethyl cellulose, methycellulose, hydroxylethylcellulose, hydroxypropylmethylcellulose, and hydroxypropylcellulose; and/or hydrophobically modified anionic, cationic, or nonionic polymers such as, but not limited to, alkyl and/or substituted hydroxyethylcellulose, lauryl dimethyl ammonium substituted epoxide of hydroxyethylcellulose, propoxylated cellulosic, xanthan, succinoglycan, or polygalactomannoses, alkyl methacrylates/crosslinked acrylic acid copolymers and/or acrylonitrile/acrylates block copolymers.

Non-limiting examples of antibacterial agents include bacitracin, phenol, benzethonium chloride, erythromycin, neomycin, tetracycline, chlortetracycline and mixtures thereof.

Non-limiting examples of sunscreens include benzophenones, bornelone, butyl PABA, cinnamidopropyl trimethyl ammonium chloride, disodium distryrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, ethylhexyl dimethyl PABA, red petrolatum, and mixtures thereof.

Non-limiting examples of preservatives include polyvinyl alcohol, phenoxyethanol, benzyl alcohol, methyl paraben, propyl paraben and mixtures thereof.

Non-limiting examples of pH adjusting agents include potassium acetate, sodium carbonate, sodium hydroxide, phosphoric acid, succinic acid, sodium citrate, citric acid, boric acid, lactic acid, sodium hydrogen carbonate and mixtures thereof.

Bleaching agents include, but are not limited to, hydrogen peroxide, perborate and persufate salts. EDTA and other aminocarboxylates may be used as sequestering agents.

Anti-dandruff agents such as zinc pyrithione, salicylic acid, climbazole, ketoconazole, sulfur piroctone olamine, selenium sulfide and mixtures thereof may also be used as an auxiliary ingredient.

The alpha hydroxy acids may exist in the keto acid form, or the ester form. Examples of such alpha hydroxy acids include glycolic acid, malic acid, pyruvic acid, mandelic acid, lactic acid, methyllactic acid, and mixtures thereof.

Also beta hydroxy acids such as salicylic acid, and derivatives thereof may be included in the compositions of the present invention. In addition, mixtures of the above alpha and beta hydroxyl acids or alpha ketoacids can be advantageously included.

The compositions described above are useful as compositions for treating keratinous substrates. These compositions include hair care products such as shampoos and conditioners, products for treating skin such as skin cleansers and personal hygiene products and products for cleaning and treating lips and nails.

For example, when the keratinous substrate being treated is hair, the compositions of the invention may impart shine, conditioning, color retention in particular when the compositions are formulated into a rinse-off product. In this case, the method of the present invention will include a rinsing step usually performed with water, after a leave-on time of the composition of at least 30 seconds.

Similar properties, along with styling, may be provided when the composition is in the form of a leave-on product.

When the keratinous substrate is skin, the compositions may impart protection from the sun (sunscreens) or provide skin benefits by serving as a carrier vehicle for skin actives (anti-acne, anti-wrinkle, etc.).

The method of treatment to be provided will depend on the keratinous substrate being targeted and, consequently, the specific ingredients contained in the composition used to effectuate the treatment. One of ordinary skill in the art will easily be able to determine these variables. Regardless of the type of treatment and/or the type of keratinous substrate chosen, the method of treatment will be performed by a composition which is clear in appearance, regardless of the degree of dilution.

EXAMPLE

The following examples are for illustrative purposes only and are not intended to limit the scope of the claims.

Example 1

Various compositions (all of them qs to 100% with water), each containing a lipophilic compound, were prepared using the ingredients listed in Table 1 below, in which all quantities as expressed as percentages by weight with regard to the total weight of the composition.

These compositions were characterized as either clear or opaque using the McFarland scale. The McFarland scale is based on the McFarland Equivalence Turbidity Standard Test (Remel, 12076 Santa Fe Drive, Lenexa, Kans. 66215, USA). McFarland standards are used most commonly in microbiology as a reference to measure turbidity of bacterial suspensions in test tubes. The standards are generally prepared suspensions of either barium chloride or latex that range from a scale of 0.5 to 4. The higher the number, the more turbid the suspension. The latex suspension standard was used in this study.

Each composition in this study was placed into a clear glass test tube and was visually compared to the McFarland standards against a white card with contrasting black lines. A composition that did not exhibit phase separation, but visually appeared to possess a McFarland turbidity standard value of greater than 0.5 (>0.5) on the McFarland scale was deemed to be opaque. Conversely, a composition that did not exhibit phase separation, but visually appeared to possess a McFarland turbidity standard value equal to, or less than 0.5 (≤0.5) on the McFarland scale was deemed to be clear.

TABLE 1

| | Organic acid | Alkoxylated polyamine | Lipophilic compound | Properties |
|---|---|---|---|---|
| 1a. | isostearic acid, 2% | Jeffamine D-230, 4% | isodecyl neopentanoate, 1.0% | ≤0.5 (clear + homogeneous) |
| 1b. | isostearic acid, 2% | — | isodecyl neopentanoate, 1.0% | Phases separated |
| 1c. | — | Jeffamine D-230, 4% | isodecyl neopentanoate, 1.0% | Phases separated |

Jeffamine D-230 belongs to the Jeffamine® D series by Hunstman of amine terminated PPGs (polypropylene glycols).

The results above show that the compositions having either the alkoxylated polyamine or the organic acid exhibited phases separation. In contrast, the compositions having both the alkoxylated polyamine and the organic acid did not exhibit phases separation and were clear (≤0.5 rating on the McFarland scale).

Example 2

Various compositions (all of them qs to 100% with water), each containing a lipophilic compound, were prepared using the ingredients listed in Table 2 below, in which all quantities as expressed as percentages by weight with regard to the total weight of the composition.

These compositions were characterized as either clear or opaque using the McFarland scale, using the same procedure as in example 1 above.

TABLE 2

| | Organic acid | Alkoxylated polyamine | Lipophilic compound | Properties |
|---|---|---|---|---|
| 1a. | laureth-5 carboxylic acid, 8% | Jeffamine D-230, 2% | retinyl palmitate, 1% | ≤0.5 (clear + homogeneous) |
| 1b. | laureth-5 carboxylic acid, 8% | — | retinyl palmitate, 1% | >0.5 (opaque) |
| 1c. | — | Jeffamine D-230, 2% | retinyl palmitate, 1% | Phases separated |

Jeffamine D-230 belongs to the Jeffamine-0 D series by Hunstman of amine terminated PPGs (polypropylene glycols).

The results above show that the compositions having either the alkoxylated polyamine or the organic acid exhibited phases separation or appeared cloudy (>0.5 rating on the McFarland scale), In contrast, the compositions having both the alkoxylated polyamine and the organic acid did not exhibit phases separation and were clear (≤0.5 rating on the McFarland scale).

Example 3

Color Retention on Artificially Colored Hair

Bleached hair swatches were colored with a commercial hair color product (Redken HiFusion™ R, 20 vol, 30 min at room temperature). The initial color L*a*b* values of the dyed hair swatches were measured in the CIELAB L*a*b* system, using a Konica Minolta Spectrophotometer 2600-D Series.

The dyed hair swatches were then treated with the following compositions (all quantities being expressed as percentages by weight) as leave-on treatments, using 6 hair swatches per composition, and using 0.4 g of composition per g of hair:
Composition 1 (clear composition): laureth-5 carboxylic acid 8.073%, Jeffamine D-230 2%, isodecyl neopentanoate 1%, water Q.S. to 100%;
Composition 2 (opaque composition): laureth-5 carboxylic acid 8.073%, isodecyl neopentanoate 1%, water Q.S. to 100%;
Composition 3 (exhibited phases separation): Jeffamine D-230 2%, isodecyl neopentanoate 1%, water Q.S. to 100%;
Composition 4 (exhibited phases separation): isodecyl neopentanoate 1%, water Q.S. to 100%;
Composition 5 (clear composition): laureth-5 carboxylic acid 8.073%, Jeffamine D-230 2%, water Q.S. to 100%;
Before its application on the hair swatches, each composition was stirred vigorously.
The treated hair swatches were rinsed with water, then shampooed (using an aqueous solution of 10% by weight of sodium laureth-2 sulfate, pH 6) for 15 seconds, using 0.4 g of shampoo per g of hair and rinsed with water for 10 seconds. The treatment and shampooing cycle was repeated up to 5 times.

The final color L*a*b* values of the hair swatches were then measured using the Konica Minolta Spectrophotometer 2600-D Series. The overall color change, represented by the ΔE value, was calculated using the equation:

$$\Delta E = \sqrt{(L^*_1 - L^*_0)^2 + (a^*_1 - a^*_0)^2 + (b^*_1 - b^*_0)^2}$$

where $L^*_0$, $a^*_0$, and $b^*_0$ are coordinates associated with initial color measurements right after coloring the hair and $L^*_1$, $a^*_1$, and $b^*_1$ are coordinates associated with the final color measurements right after the 5$^{th}$ treatment-shampooing cycle. The L coordinate represents the color intensity of the swatch being tested based on a dark to light scale. The a coordinate represents the color position between red and green. The b coordinate represents the color position between yellow and blue. A higher ΔE value would signify a greater color change or a greater color loss between initial and final color measurements.

The following changes in total color (ΔE) are shown below.

| Composition | ΔE after 5 shampoos |
|---|---|
| 1 | 11.70 |
| 2 | 15.95 |
| 3 | 13.48 |
| 4 | 16.89 |
| 5 | 17.70 |

The results above show that the artificially colored hair swatches treated with the inventive composition significantly retained more color (less color loss) than all other compositions. Therefore, the composition of the present invention imparts a color protection to hair, significantly better than any other compositions lacking one or more of its components.

Example 4

Color Retention on Artificially Colored Hair

Bleached hair swatches were colored with a commercial hair color product (Redken HiFusion™ R, 20 vol, 30 min at room temperature). The initial color L*a*b* values of the dyed hair swatches were measured in the CIELAB L*a*b* system, using a Konica Minolta Spectrophotometer 2600-D Series.

Six dyed hair swatches were then treated with the following composition (quantities expressed as percentages by weight) as leave-on treatment, using 0.4 g of composition per g of hair:

Test composition (clear composition): isostearic acid 2%, Jeffamine D-230 4%, isodecyl neopentanoate 1%, water qs to 100%.

The treated hair swatches were rinsed with water, then shampooed (using an aqueous solution of 10% by weight of sodium laureth-2 sulfate, pH 6) for 15 seconds, using 0.4 g of shampoo per g of hair and rinsed with water for 10 seconds. The treatment and shampooing cycle was repeated up to 5 times (test treatment).

As control treatment, six dyed hair swatches were shampooed 5 times as indicated above, without treatment with the Test composition.

In each case, the final color L*a*b* values of the hair swatches were measured and the overall color change ΔE was calculated as indicated in example 3 above.

The following changes in total color (ΔE) are shown below.

| Treatment | ΔE after 5 shampoos |
|---|---|
| Test treatment | 12.05 |
| Control treatment | 15.00 |

The results above show that the artificially colored hair swatches treated with the inventive test treatment significantly retained more color (less color loss) than the hair swatches treated using the control treatment. Therefore, the composition of the present invention imparts a color protection to the hair.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. A composition comprising:
(a) at least one alkoxylated polyamine chosen from compounds corresponding to formula (I):

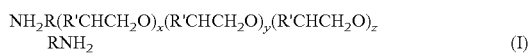

(I)

wherein R represents a —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted;

x, y, and z independently of one another, represent numbers of from 0 to 100;

R' represents hydrogen, or an alkyl group; and the sum of x+y+z is at least 1;

compounds corresponding to formula (II):

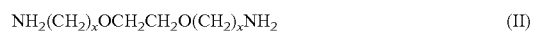

(II)

wherein x is 2 or 3;

compounds corresponding to formula (III):

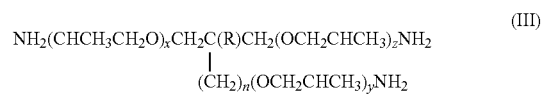

(III)

wherein R is hydrogen or —C$_2$H$_5$, n=0 or 1, and x, y, and z independently of one another, represent numbers of from 0 to 100 and the sum of x+y+z is at least 1; and compounds of formulas (IV) and (V) hereunder:

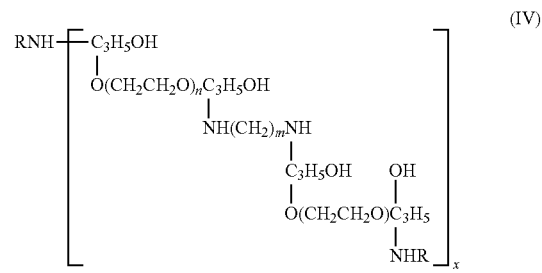

(IV)

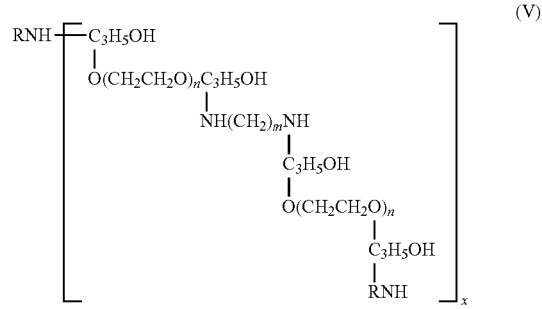

(V)

wherein

R in formula (IV) represents the alkyl group derived from tallow and R in formula (V) represents the alkyl group derived from coconut oil;

n in both formulas (IV) and (V) has a total value ranging from 10 to 20;

m in both formulas (IV) and (V) has a value ranging from 2 to 6; and x in both formulas (IV) and (V) has a value ranging from 2 to 4;

(b) at least one organic acid chosen from alkoxylated monoacid compounds corresponding to formula (IB):

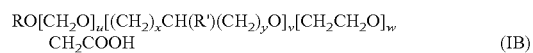

(IB)

wherein:
R is a hydrocarbon radical containing from 6 to 40 carbon atoms;
u, v and w, independently of one another, represent numbers of from 0 to 60, provided that the sum u+v+w is greater than 0;
x and y, independently of one another, represent numbers of from 0 to 13, where the sum x+y is greater than or equal to 0;
R' represents hydrogen or an alkyl group;
fatty monocarboxylic acid compounds corresponding to formula (IA):

$$RCOOH \qquad (IA)$$

wherein R is a hydrocarbon radical containing at least 6 carbon atoms; and
fatty phosphoric acid compounds corresponding to formula (IIA):

$$R\text{—}O\text{—}P(O)(OH)_2 \qquad (IIA)$$

wherein R is a hydrocarbon radical containing at least 6 carbon atoms;
(c) at least one lipophilic compound; and
(d) at least one solvent comprising water;
wherein the ratio of the amine number of the at least one alkoxylated polyamine to the acid number of the at least one organic acid is from 1:10 to 10:1.

2. The composition of claim 1, wherein the at least one alkoxylated polyamine is present in an amount of from 0.5 to 15% by weight, based on the total weight of the composition.

3. The composition of claim 1, wherein the at least one alkoxylated polyamine is present in an amount of from 0.5 to 15% by weight, based on the total weight of the composition.

4. The composition of claim 1, wherein the at least one alkoxylated polyamine is present in an amount of from 0.5 to 10% by weight, based on the total weight of the composition.

5. The composition of claim 1, wherein in formula (IIA) R is a hydrocarbon radical containing from 8 to 30 carbon atoms.

6. The composition of claim 1, wherein in formula (IIA) R is a hydrocarbon radical containing from 8 to 30 carbon atoms.

7. The composition of claim 1, wherein in formula (IB) R is a hydrocarbon radical containing from 8 to 30 carbon atoms.

8. The composition of claim 1, wherein in formula (IB) R is a hydrocarbon radical containing from 12 to 24 carbon atoms.

9. The composition of claim 1, wherein the at least one organic acid is present in an amount of from 0.1 to 50% by weight, based on the total weight of the composition.

10. The composition of claim 1, wherein the at least one organic acid is present in an amount of from 0.5 to 30% by weight, based on the total weight of the composition.

11. The composition of claim 1, wherein the at least one organic acid is present in an amount of from 1 to 20% by weight, based on the total weight of the composition.

12. The composition of claim 1, wherein the ratio of the amine number of the at least one alkoxylated polyamine to the acid number of the at least one organic acid is 1:4.

13. The composition of claim 1, wherein the ratio of the amine number of the at least one alkoxylated polyamine to the acid number of the at least one organic acid is from 1:5 to 5:1.

14. The composition of claim 1, wherein the ratio of the amine number of the at least one alkoxylated polyamine to the acid number of the at least one organic acid is from 1:2 to 2:1.

15. The composition of claim 1, wherein the at least one lipophilic compound is chosen from oils, fatty esters, hydrocarbon oils, silicones, waxes, fatty alcohols, lipophilic vitamins and esters thereof, organic sunscreens, phospholipids, and mixtures thereof.

16. The composition of claim 1, wherein the at least one lipophilic compound is present in an amount of from 0.1 to 50% by weight, based on the total weight of the composition.

17. The composition of claim 1, wherein the at least one lipophilic compound is present in an amount of from 0.1 to 30% by weight, based on the total weight of the composition.

18. The composition of claim 1, wherein the at least one lipophilic compound is present in an amount of from 0.5 to 15% by weight, based on the total weight of the composition.

19. The composition of claim 1, wherein the solvent is present in an amount from 10 to 95% by weight, based on the total weight of the composition.

20. The composition of claim 1, wherein the solvent is present in an amount from 50 to 85% by weight, based on the total weight of the composition.

21. The composition of claim 1, wherein the solvent is present in an amount from 60 to 80% by weight, based on the total weight of the composition.

22. The composition of claim 1, wherein the solvent comprises at least 20% by weight of water, based on the total weight of the solvent.

23. The composition of claim 1, wherein the solvent further comprises at least one $C_1$-$C_4$ alcohol.

24. A method of making a clear composition involving the steps of:
(a) providing at least one alkoxylated polyamine chosen from compounds corresponding to formula (I):

$$NH_2R(R'CHCH_2O)_x(R'CHCH_2O)_y(R'CHCH_2O)_zRNH_2 \qquad (I)$$

wherein R represents a —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted;
x, y, and z independently of one another, represent numbers of from 0 to 100;
R' represents hydrogen, or an alkyl group; and
the sum of x+y+z is at least 1;
compounds corresponding to formula (II):

$$NH_2(CH_2)_xOCH_2CH_2O(CH_2)_xNH_2 \qquad (II)$$

wherein x is 2 or 3;
compounds corresponding to formula (III):

$$NH_2(CHCH_3CH_2O)_xCH_2C(R)CH_2(OCH_2CHCH_3)_2NH_2 \\ | \\ (CH_2)_n(OCH_2CHCH_3)_yNH_2 \qquad (III)$$

wherein R is hydrogen or —C$_2$H$_5$,
n=0 or 1, and
x, y, and z independently of one another, represent numbers of from 0 to 100 and the sum of x+y+z is at least 1; and compounds of formulas (IV) and (V) hereunder:

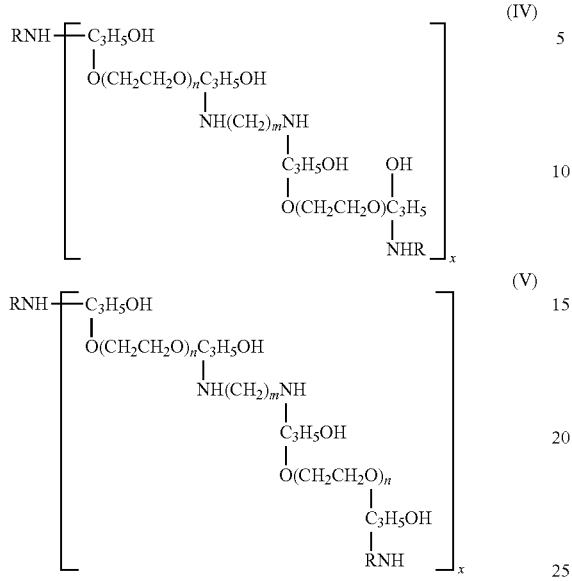

wherein
R in formula (IV) represents the alkyl group derived from tallow and R in formula (V) represents the alkyl group derived from coconut oil;
n in both formulas (IV) and (V) has a total value ranging from 10 to 20;
m in both formulas (IV) and (V) has a value ranging from 2 to 6; and
x in both formulas (IV) and (V) has a value ranging from 2 to 4;
(b) providing at least one organic acid chosen from alkoxylated monoacid compounds corresponding to formula (IB):

$$RO[CH_2O]_u[(CH_2)_yO]_v[CH_2CH_2O]_w CH_2COOCH \quad (IB)$$

wherein:
R is a hydrocarbon radical containing from 6 to 40 carbon atoms;
u, v and w, independently of one another, represent numbers of from 0 to 60, provided that the sum u+v+w is greater than 0;
x and y, independently of one another, represent numbers of from 0 to 13, where the sum x+y is greater than or equal to 0;
R' represents hydrogen or an alkyl group:
fatty monocarboxylic acid compounds corresponding to formula (IA):

$$RCOOH \quad (IA)$$

wherein R is a hydrocarbon radical containing at least 6 carbon atoms; and
fatty phosphoric acid compounds corresponding to formula (IIA):

$$R-O-P(O)(OH)_2 \quad (IIA)$$

wherein R is a hydrocarbon radical containing at least 6 carbon atoms;
(c) providing at least one lipophilic compound;
(d) providing at least one solvent comprising water; and
(e) mixing the compounds as defined in steps (a) to (d) to form a composition that is clear in appearance;

wherein the ratio of the amine number of the at least one alkoxylated polyamine to the acid number of the at least one organic acid is from 1:10 to 10:1.

25. A method of cosmetic treatment of a keratinous substrate involving the step of applying onto said keratinous substrate a composition comprising:
(a) at least one alkoxylated polyamine chosen from compounds corresponding to formula (I):

$$NH_2R(R'CHCH_2O)_x(R'CHCH_2O)_y(R'CHCH_2O)_z RNH_2 \quad (I)$$

wherein R represents a —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted;
x, y, and z independently of one another, represent numbers of from 0 to 100;
R' represents hydrogen, or an alkyl group; and
the sum of x+y+z is at least 1;
compounds corresponding to formula (II):

$$NH_2(CH_2)_xOCH_2CH_2O(CH_2)_xNH_2 \quad (II)$$

wherein x is 2 or 3;
compounds corresponding to formula (III):

$$NH_2(CHCH_3CH_2O)_xCH_2C(R)CH_2(OCH_2CHCH_3)_2NH_2 \\ | \\ (CH_2)_n(OCH_2CHCH_3)_yNH_2 \quad (III)$$

wherein R is hydrogen or —C$_2$H$_5$,
n=0 or 1, and
x, y, and z independently of one another, represent numbers of from 0 to 100 and the sum of x+y+z is at least 1; and
compounds of formulas (IV) and (V) hereunder:

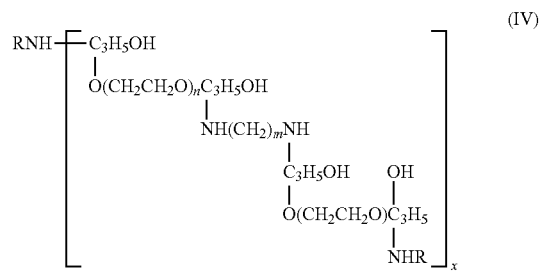

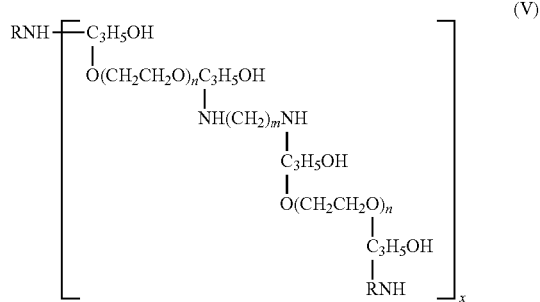

wherein
R in formula (IV) represents the alkyl group derived from tallow and R in formula (V) represents the alkyl group derived from coconut oil;

n in both formulas (IV) and (V) has a total value ranging from 10 to 20;

m in both formulas (IV) and (V) has a value ranging from 2 to 6; and x in both formulas (IV) and (V) has a value ranging from 2 to 4;

(b) at least one organic acid chosen from alkoxylated monoacid compounds corresponding to formula (IB):

$$RO[CH_2O]_u[(CH_2)_xCH(R')(CH_2)_yO]_v[CH_2CH_2O]_w CH_2COOH \quad (IB)$$

wherein:

R is a hydrocarbon radical containing from 6 to 40 carbon atoms;

u, v and w, independently of one another, represent numbers of from 0 to 60, provided that the sum u+v+w is greater than 0;

x and y, independently of one another, represent numbers of from 0 to 13, where the sum x+y is greater than or equal to 0;

R' represents hydrogen or an alkyl group;

fatty monocarboxylic acid compounds corresponding to formula (IA):

$$RCOOH \quad (IA)$$

wherein R is a hydrocarbon radical containing at least 6 carbon atoms; and fatty phosphoric acid compounds corresponding to formula (IIA):

$$R{-}O{-}P(O)(OH)_2 \quad (IIA)$$

wherein R is a hydrocarbon radical containing at least 6 carbon atoms;

(c) at least one lipophilic compound; and (d) at least one solvent comprising water;

wherein the ratio of the amine number of the at least one alkoxylated polyamine to the acid number of the at least one organic acid is from 1:10 to 10:1.

26. The method of claim 25, wherein the at least one alkoxylated polyamine is present in an amount of from 0.1 to 50% by weight, based on the total weight of the composition.

27. The method of claim 25, wherein the at least one organic acid is present in an amount of from 0.1 to 50% by weight, based on the total weight of the composition.

28. The method of claim 25, wherein the ratio of the amine number of the at least one alkoxylated polyamine to the total acid number of the at least one organic acid is from 1:5 to 5:1.

29. The method of claim 25, wherein the at least one lipophilic compound is chosen from oils, fatty esters, hydrocarbon oils, silicones waxes, fatty acids and salts thereof, fatty alcohols, lipophilic vitamins and esters thereof, organic sunscreens, phospholipids, and mixtures thereof.

30. The method of claim 25, wherein the solvent is present in an amount from 10 to 95% by weight, based on the total weight of the composition.

31. The composition of claim 1, wherein the at least one organic acid is selected from the group comprising Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid.

32. The composition of claim 1, wherein the at least one alkoxylated polyamine is selected from the group comprising diamine compounds of amine terminated polypropylene glycols and polyether diamine based compounds with a predominantly polyethylene glycol backbone.

33. A composition comprising:
(a) at least one alkoxylated polyamine present in an amount of from about 0.5% to about 10% by weight, based on the total weight of the composition and selected from the group comprising diamine compounds of amine terminated polypropylene glycols and polyether diamine based compounds with a predominantly polyethylene glycol backbone;
(b) at least one organic acid present in an amount of from about 1% to about 20% by weight, based on the total weight of the composition and selected from the group comprising Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid;
(c) at least one lipophilic compound; and
(d) at least one solvent comprising water;
wherein the ratio of the amine number of the at least one alkoxylated polyamine to the acid number of the at least one organic acid is from 1:5 to 5:1.

* * * * *